United States Patent
Lannoy

(10) Patent No.: US 9,039,647 B2
(45) Date of Patent: *May 26, 2015

(54) REGIONAL CITRATE ANTICOAGULATION

(75) Inventor: Jean-Michel Lannoy, Anstaing (FR)

(73) Assignee: NIKKISO CO., LTD., Tokyo (JP)

(*) Notice: Subject to any disclaimer, the term of this patent is extended or adjusted under 35 U.S.C. 154(b) by 936 days.

This patent is subject to a terminal disclaimer.

(21) Appl. No.: 13/174,217

(22) Filed: Jun. 30, 2011

(65) Prior Publication Data

US 2011/0264025 A1  Oct. 27, 2011

Related U.S. Application Data

(63) Continuation of application No. 11/525,800, filed on Sep. 21, 2006, now Pat. No. 8,372,025.

(60) Provisional application No. 60/719,718, filed on Sep. 22, 2005.

(51) Int. Cl.
    *A61M 37/00* (2006.01)
    *A61M 1/36* (2006.01)
    *A61M 1/16* (2006.01)

(52) U.S. Cl.
    CPC ............. *A61M 1/3672* (2013.01); *A61M 1/16* (2013.01); *A61M 1/3609* (2014.02)

(58) Field of Classification Search
    USPC .............. 604/4.01–6.16, 7–10; 210/645–650; 424/601, 630, 639, 646, 663, 682
    See application file for complete search history.

(56) References Cited

U.S. PATENT DOCUMENTS

| 7,029,456 B2* | 4/2006 | Ware et al. ................. 604/131 |
| 8,372,025 B2 | 2/2013 | Lannoy |
| 2002/0004530 A1* | 1/2002 | Warnock .................. 514/574 |

OTHER PUBLICATIONS

Chinese Office Action issued on Oct. 11, 2012 for corresponding Chinese Patent Application No. 200680018928.6.
Manns et al., The acu-menTM: A new device for continuous renal replacement therapy in actue renal failure, Kidney International, 1998, pp. 268-74, vol. 54.
Jun. 19, 2014 Office Action issued in U.S. Appl. No. 13/174,192.
European Office Action issued Oct. 21, 2013 in corresponding European Patent Application No. 06 804 078.1.
Oct. 7, 2014 Office Action issued in U.S. Appl. No. 13/174,192.

* cited by examiner

*Primary Examiner* — Philip R Wiest
(74) *Attorney, Agent, or Firm* — Oliff PLC

(57) ABSTRACT

A system or method automates and optimizes citrate anticoagulant supplementation in a blood filtration circuit during CRRT. A processor-based control system interfaces with a blood filtration circuit to detect patient blood flow into the circuit, detect fluid loss through a hemofilter, and sense vital electrolyte concentrations in the blood flow, and in response, control the addition of citrate, substitution fluid, and electrolyte supplements to ensure stability of plasma concentrations in post-dilution flow returned to the patient. The controller executes the method embodied as process control algorithms for calculating an optimal citrate flow rate as a function of selected, detected, and calculated system parameters. Citrate may be added to the circuit separately, or as part of a substitution solution or a dialysate.

11 Claims, 10 Drawing Sheets

REGIONAL CITRATE ANTICOAGULATION

PRIORITY CLAIM AND CROSS-REFERENCE TO RELATED APPLICATIONS

The present Application for Patent is a continuation application of and claims priority to U.S. patent application Ser. No. 11/525,800 entitled "Automation and optimization of CRRT treatment using regional citrate anticoagulation" filed on Sep. 21, 2006, expressly incorporated herein by reference, which is a non-provisional of and claims priority to Provisional Application 60/719,718 entitled "Citrate expert system" filed on Sep. 22, 2005, expressly incorporated herein by reference. The present Application is related to and hereby incorporates by reference the following commonly owned patent publications: "REGIONAL CITRATE ANTICOAGULATION," application Ser. No. 13/174,217, and "FLOW BALANCING SYSTEM AND METHOD, ESPECIALLY FOR CITRATE," application Ser. No. 13/185,147.

BACKGROUND

1. Field

The present invention relates generally to blood filtration and to continuous renal replacement therapy (CRRT). More specifically, the invention relates to automatic control and optimization of citrate flow rate, and fluid exchange flow rates, during CRRT therapy.

2. Background

There are many continuous renal replacement therapies (CRRT) commonly used for treating patients suffering loss or impairment of natural renal functions. In a typical CRRT, blood is removed from a patient and pumped through an extracorporeal circuit that includes an artificial kidney. The artificial kidney contains a hemofilter or semi-permeable membrane. The blood is circulated along one surface of the membrane, and a dialysate fluid is circulated along the opposing surface. Through osmosis or differential pressure, the hemofilter allows migration of soluble waste and water from the blood across the membrane and into the dialysate solution. The filtered blood is then returned to the patient.

Generally, CRRT therapies remove water and waste solute at a slow and steady rate over long periods of time to ensure hemodynamic stability. In order maintain a constant total blood volume of a patient undergoing CRRT, a substitution fluid is introduced into the bloodstream in the extracorporeal circuit. Depending on the type of CRRT used, the substitution fluid may be introduced either upstream or downstream of the hemofilter. The composition of the substitution fluid, the composition of the dialysate, the flow rates of blood and dialysate, the pressure gradient across the membrane, and the composition of the membrane all contribute to the effectiveness of CRRT treatment.

Some of the more common CRRT methods in use today include ultrafiltration, hemodialysis, hemofiltration, and hemodiafiltration. Ultrafiltration describes any method that relies on movement of water from blood across a semi-permeable membrane, due to a pressure gradient across the membrane. Hemodialysis involves convective diffusion of solutes from blood across a semi-permeable membrane into a volume of dialysate flow. The dialysate is made to flow on one side of the membrane in a direction opposite the flow of blood on the other side of the membrane to maintain a concentration gradient across the membrane. Hemofiltration operates without a dialysate, and instead uses a positive hydrostatic pressure to drive water and solutes across a more porous membrane. Hemodiafiltration is a combination of hemodialysis and hemofiltration methods. In the literature, these therapies may be more specifically defined according to the patient access and return sites, and to fluid transfer characteristics, e.g. continuous venous-venous hemofiltration (CVVH), continuous venous-venous hemodialysis (CVVHD), continuous venous-venous hemodiafiltration (CVVHDF), high volume hemofiltration (HVHF), etc.

One problem common to all CRRT therapies is blood coagulation in the extracorporeal circuit, and primarily across the membrane within the artificial kidney. To prevent blood coagulation, an anticoagulant is typically added to the bloodstream in the extracorporeal circuit upstream of the hemofilter. Historically heparin has been used as a preferred anticoagulant, and more recently, citrate ions in the form of trisodium citrate have been proven effective in CRRT as an anticoagulant. A substitution fluid for use in hemofiltration that uses citrate as an anticoagulant, as well as additional background on citrate anticoagulation and CRRT therapies, are disclosed in U.S. Pat. No. 6,743,191, which is fully incorporated herein by reference.

One significant concern arising from the use of citrate as an anticoagulant is its effect on blood electrolyte levels. Citrate ions bond to positively charged electrolytes such as calcium and magnesium, thus, any passage of the citrate through the hemofilter and into the dialysate depletes these electrolytes from the bloodstream. If the proper electrolyte levels are not maintained during CRRT, in the worst case, hypocalcemia or hypomagnesemia may be induced in the patient and cause life-threatening complications.

Previous methodologies have been proposed for fixing citrate flow rate as a function of blood flow rate during CRRT. However, the results vary widely, and provide only general guidelines that do not necessarily optimize treatment in a specific case. Oudemans-van Straaten, H. M., "Guidelines for Anticoagulation in Continuous Venovenous Hemofiltration (CVVH)," recommends a citrate flow rate (CFR) of 35 mmol/h for a blood flow rate (BFR) of 200 ml/min. The "Monza protocol", promoted by the Italian Association of Pediatric Hematology and Oncology (AIEOP) et al., recommends a CFR of 52.5 mmol/h for the same BFR. Strake, (no citation available) extrapolated to 200 ml/min BFR, recommends a CFR of 33.3 mmol/h. Mehta, R. L. et al., "Regional Citrate Anticoagulation for Continuous Arteriovenous Haemodialysis in Critically Ill Patients," Kidney Int. 1990, Vol. 38(5), pp. 976-981, extrapolated to 200 ml/min BFR, recommends a CFR of 38.1 mmol/h. Kutsogiannis, D. J. et al., "Regional Citrate Anticoagulation in Continuous Venovenous Haemodiafiltration," Am. J. Kidney Dis. 2000, Vol. 35(5), pp. 802-811, extrapolated to 200 ml/min BFR, recommends 40 mmol/h CFR. Palsson, R. et al., "Regional Citrate Anticoagulation in Continuous Venovenous Haemofiltration in Critically Ill Patients with a High Risk of Bleeding," Kidney Int. 1999, Vol. 53, pp. 1991-1997, extrapolated to 200 ml/min BFR, recommends a CFR of 20.6 mmol/h. Tolwani, A. J. et al., "Simplified Citrate Anticoagulation for Continuous Renal Replacement Therapy," Kidney Int. 2001, Vol. 60, pp. 370-374, extrapolated to 200 ml/min BFR, recommends a CFR of 28 mmol/h. Cointault, O. et al., "Regional Citrate Anticoagulation in Continuous Venovenous Haemodiafiltration Using Commercial Solutions," Nephrol. Dial. Transplant., January 2004, Vol. 19(1), pp. 171-178, extrapolated to 200 ml/min BFR, recommends a CFR of 45.6 mmol/h. Taken as a whole, the available literature provides no consensus for optimizing regional citrate anticoagulation.

During administration of CRRT, regardless of CRRT type and protocol, multiple parameters in the blood filtration circuit must be maintained under strict control to ensure patient stability. Blood chemistry, blood and fluid flow rates, dialysate concentration, substitution fluid concentration, ultrafiltration rate, filter pressure drop, and fluid temperatures and pressures are some of the many parameters that must be carefully monitored and adjusted to ensure proper administration of the therapy. Depending on the particular blood chemistry and physical condition of the patient, the various flow rates and concentrations may need to be more finely adjusted. A source of citrate ions introduced in the system adds another dimension of complexity. What is needed is an expert system for controlling these parameters according to the needs of the individual patient.

SUMMARY

The present invention provides a system or method for automating and optimizing citrate anticoagulant supplementation in a blood filtration circuit during CRRT. In an extracorporeal blood filtration circuit such as a dialysis machine, one embodiment of the invention may comprise a control system and related components that interface with such an existing machine, or it may comprise the entire extracorporeal fluid mechanical circuit and attendant control system. One embodiment of a method according the invention may comprise a series of process steps stored in a computer program for controlling the system, its components, and instrumentation, or for providing a health care technician with information for effecting manual controls.

A system according to one embodiment of the invention may comprise a blood flow detector for detecting a flow of blood from a patient access site into the blood filtration circuit, an electrolyte sensor for detecting a concentration of various electrolytes present in the blood flow, a source of citrate solution having a selected citrate concentration, a citrate pump for causing flow of the citrate solution into the blood filtration circuit, and a controller such as a computer processor coupled to memory, for controlling the flow from the citrate pump. In one aspect, the controller may effect citrate pump flow by executing a control algorithm that calculates an optimal citrate flow rate as a function of the detected blood flow, the sensed electrolyte concentration, and the selected citrate concentration, each of which may be transmitted as an input signal to the controller.

In various embodiments, the electrolyte sensor may sense one or more vital electrolytes such as calcium and magnesium ions that may be lost from patient blood plasma through the filtration process. An embodiment of the system may be further configured with a source of supplemental electrolyte solution, an electrolyte pump, and related instrumentation for detecting fluid loss rate through a hemofilter and for controlling electrolyte solution flow. Another embodiment of the system may be further configured with a source of substitution solution, a substitution solution pump, related instrumentation, and control algorithms for adding pre-dilution and/or post-dilution flow of substitution solution to the blood flow. In other embodiments, the system may add citrate to the blood flow as part of a substitution solution, or with a dialysate. Based on selected, detected, or calculated system parameters, the controller may optimize citrate flow, electrolyte flow, post-dilution flow, and other parameters to maintain a desired quality and flow of blood plasma returning to the patient.

A method according to one embodiment of the invention optimizes citrate anticoagulant supplementation in a blood filtration circuit during CRRT through execution of process steps. These steps may include detecting a flow rate of blood from a patient access site, detecting electrolyte concentration in the blood flow, adding to the blood filtration circuit a flow of citrate solution having a known citrate concentration, and controlling the flow rate of the citrate solution as a function of the detected blood flow rate, the detected electrolyte concentration, and the known citrate concentration. Other embodiments may include additional process steps for detecting specific vital electrolytes, detecting fluid loss rates through the hemofilter, detecting supplemental electrolyte solution flow rates, detecting substitution fluid flow rates, and in response, controlling system flow rates as a function of selected, detected, or calculated system parameters to maintain a desired quality and flow of blood plasma returning to the patient. In alternative embodiments, a method may control the addition of citrate anticoagulant as part of a pre-dilution substitution solution, or as part of a dialysate. Any of the method steps may be embodied as software in computer readable media executable by a processor to effect automatic control of a CRRT system.

BRIEF DESCRIPTION OF THE DRAWINGS

The features, objects, and advantages of the invention will become more apparent from the detailed description set forth below when taken in conjunction with the drawings, wherein.

DETAILED DESCRIPTION

An exemplary embodiment of the present invention provides an expert method or system for optimizing a CRRT therapy that uses a regional citrate anticoagulant. Exemplary embodiments of methods presented herein calculate optimal flow rates for the introduction or passage of various fluids through an extracorporeal fluid mechanical circuit employed for effecting CRRT. Flow rate calculations may be performed using formulas that rely on inputs representing fixed or measured parameters operating throughout the circuit. Calculated results may be manually transmitted by a technician reading the results and adjusting flow rates accordingly, or may be automatically transmitted from a central processor as control signals in a system according to an embodiment of the invention that includes the processor, the calculation software, and the extracorporeal circuit.

Figure 1:
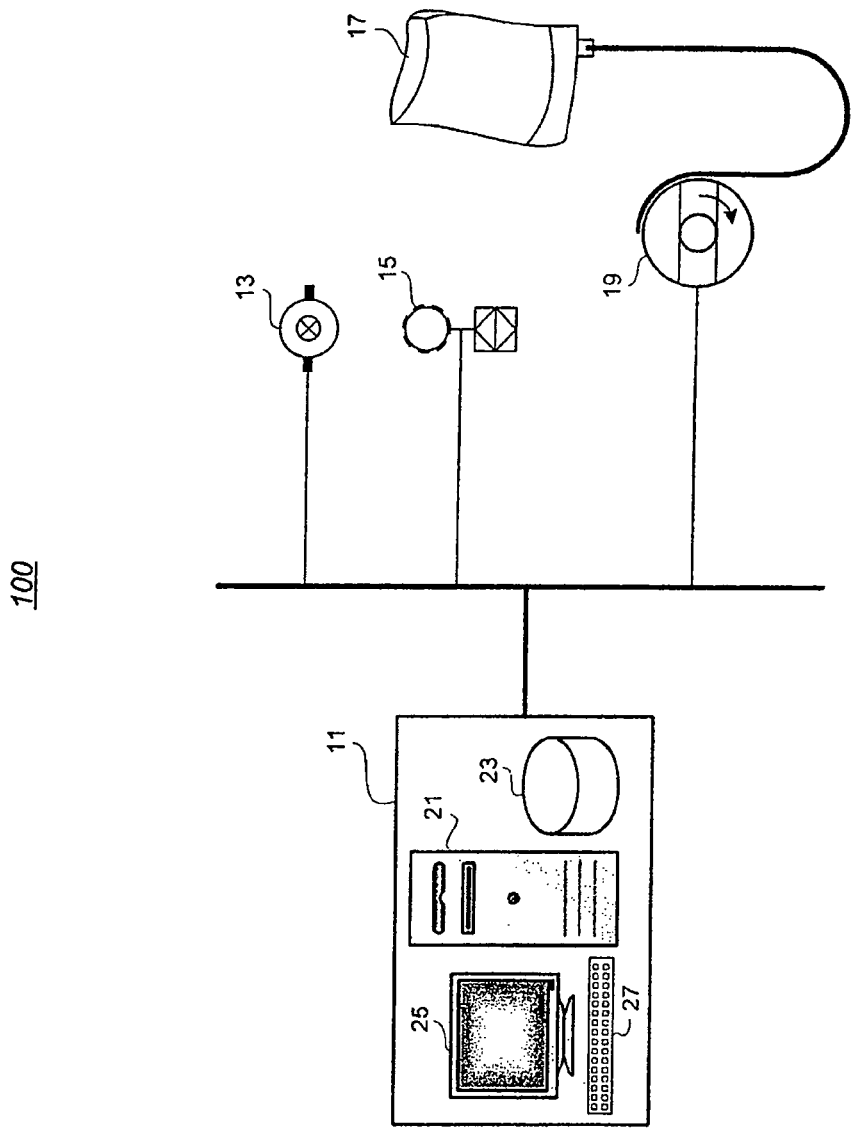
FIG. 1 shows a schematic diagram of a system according to the invention for optimizing CRRT treatment using regional citrate anticoagulation.

FIG. 1 shows a schematic diagram of one embodiment of a system 100 according to the invention. System 100 may be used in combination with other CRRT equipment (such as a dialysis machine) to provide regional citrate anticoagulation. As such, some or all of the components of system 100 may form an integral part of the extracorporeal circuit. A central computer or controller 11 may allow a user to manually or automatically control other components within system 100. In basic form, these may include a blood flow detector 13, an electrolyte sensor 15, a source of citrate solution 17, and a citrate pump 19. Controller 11 communicates with each of these components via signal line 12. Signal line 12 may be made up of one or more electrical cables or groups of electrical cables or buses suitable for analog or digital signal transmission. In another embodiment, bus 12 may represent one or more wireless links.

Controller 11 may include a CPU 21, which may be a general purpose computer, personal computer, or other suitable microprocessor-based component or microcontroller known in the art. A computer-readable memory 23, accessible by CPU 21, may be integral to CPU 21 or may be separately coupled thereto. Memory 23 may include software, executable by CPU 21, for effecting various controller functions including receiving system input signals and transmitting output control signals. Memory 23 may also include any conventional operating system software essential for basic computing operations. Controller 11 may further include peripheral devices such as a display unit 25 and a user interface 27. Display unit 25 and user interface 27 may assist a user during manual operation of the system. For example, controller 11 may perform a calculation for determining a flow rate within the extracorporeal circuit, and may display the results of the calculation on display unit 25. A user reading these results may then adjust a circuit component manually. Or, the user may adjust the component remotely by manual entry of keystrokes on user interface 27.

Blood flow detector 13 detects the flow or flow rate of blood taken from a patient access site during CRRT. Blood flow detector 13 may be any commercial detector known in the art and commonly used for this purpose, such as a non-invasive infrared or ultrasonic Doppler type detector. In one embodiment, blood flow detector 13 may include a pressure sensor for detecting a differential pressure between two points in the blood flow, for derivation of a signal representative of the blood flow.

Electrolyte sensor 15 may be any sensor or detection system capable of analyzing blood for the presence of specific electrolytes such as ions of bicarbonate, calcium, chloride, copper, glucose, iron, magnesium, manganese, phosphate, potassium, sodium, or zinc. For example, electrolyte sensor 15 may be an electrochemical sensor such as a continuous blood gas analyzer, an ionic conductive ceramic sensor, an ion conductive electrode, or a sensor employing an ion sensitive field effect transistor. Alternatively, electrolyte sensor 15 may include a mass spectrometer for analyzing discrete samples taken from the blood flow at predetermined time intervals. In one embodiment, electrolyte sensor 15 senses calcium ion concentration and magnesium ion concentration.

Citrate solution 17 may be any suitable container for containing a volume of citrate ions in solution. A transfusion or infusion bag containing a solution of citric acid or trisodium citrate of a selected concentration may be used for this purpose. Citrate pump 19 may be connected to draw a flow from citrate solution 17 for supplementing the blood flow in the extracorporeal circuit. Citrate pump 19 may be any suitable commercially available pump commonly used in the medical field for pumping blood, such as a diaphragm, centrifugal, or peristaltic pump.

System 100 operates by controller 11 receiving input signals from blood flow detector 13 and electrolyte sensor 15, representing blood flow and electrolyte concentration, respectively. Controller 11 may then calculate an optimal citrate flow rate as a function of the detected blood flow, the sensed electrolyte concentration, and the selected citrate concentration. In one embodiment, CPU 21 performs this calculation by executing an algorithm stored in memory 23. Controller 11 then transmits an output signal representing the optimal citrate flow rate to citrate pump 19, which, in response to receiving the output signal, adjusts its speed to achieve the optimal flow rate.

In one embodiment of a system according to the invention, the algorithm for calculating optimal citrate flow rate, E, may be expressed as $E=f(A, B, C, D)$, where A is a blood flow rate detected by blood flow detector 13, B is a calcium ion concentration detected by electrolyte sensor 15, C is a citrate concentration selected for citrate solution 17, and D is a magnesium ion concentration detected by electrolyte sensor 15. In one embodiment, E may be expressed as:

$$E=A\times(B+D)/C \quad (1)$$

In another embodiment, citrate solution 17 may contain a selected citric acid concentration and a selected trisodium citrate concentration. In this embodiment, controller 11 may calculate an optimal citrate flow rate a function of blood flow, electrolyte concentration, citric acid concentration, and trisodium citrate concentration. For example, to optimize citrate flow rate during CRRT, controller 11 may control the flow rate $E=f(A, B, C, D, G)$ of citrate pump 19 according to:

$$E=A\times(B+D)/(C+G) \quad (2)$$

where A is a blood flow rate detected by blood flow detector 13, B is a calcium ion concentration detected by electrolyte sensor 15, C is a citric acid concentration selected for citrate solution 17, D is a magnesium ion concentration detected by electrolyte sensor 15, and G is a trisodium citrate concentration selected for citrate solution 17.

Figure 2:
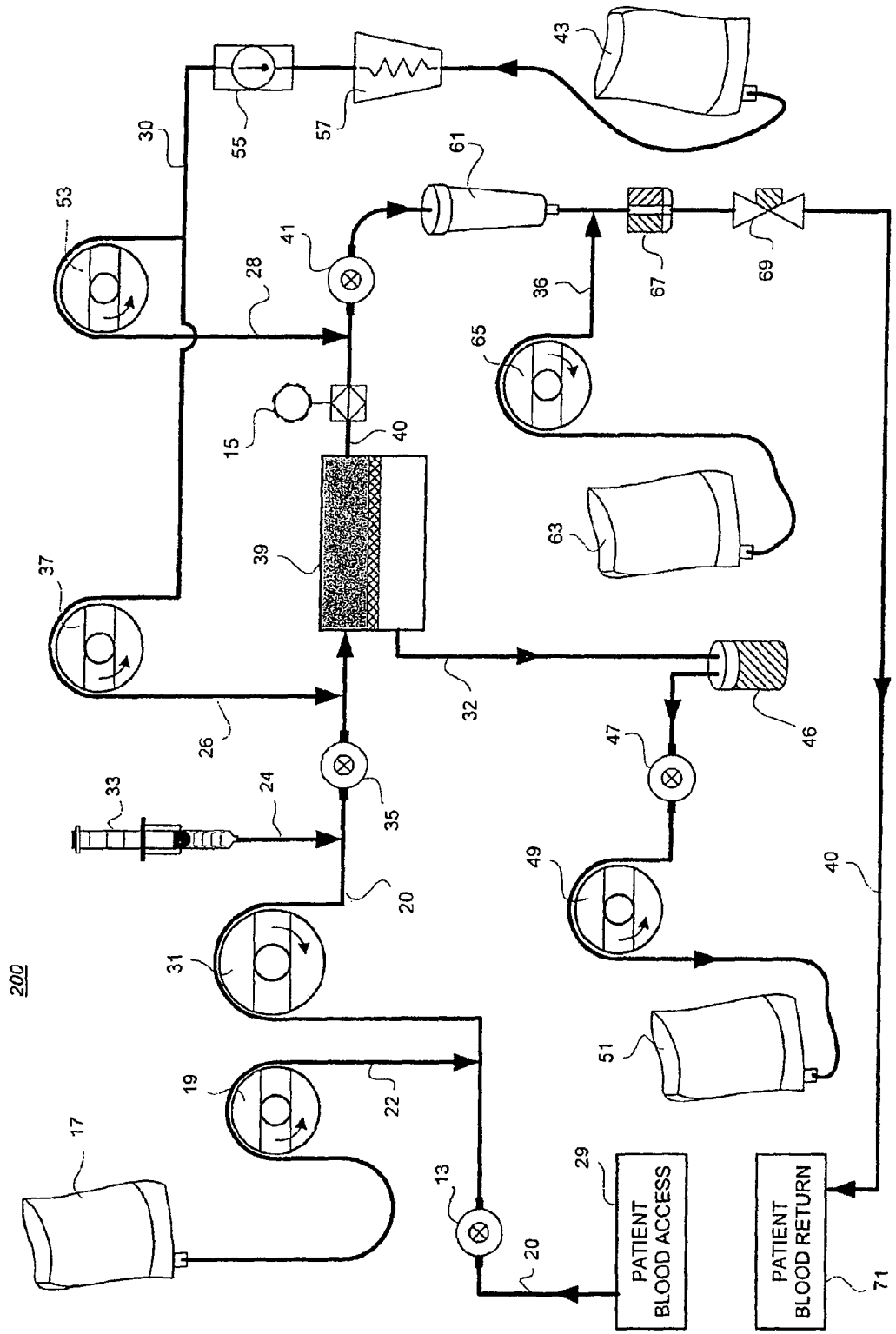
FIG. 2 is a diagram of a blood filtration circuit for CRRT treatment, equipped for automated control using a system according to the invention.

FIG. 2 illustrates another embodiment of the invention as a system 200, equipped for automated control, wherein citrate is added as a pre-dilution anticoagulant solution. System 200 also includes additional components in a blood filtration or artificial kidney circuit that may be used, for example, in CVVH or HVHF CRRT therapies.

A patient blood access site 29 provides a source for drawing a flow of unfiltered blood 20 from a patient into the extracorporeal circuit. A blood pump 31 provides the mechanical force required for sustaining a continuous flow of blood. Like citrate pump 19, blood pump 31 may be any conventional pump known in the medical arts and suitable for the purpose, such as a peristaltic pump. Blood flow detector 13, which may be a pressure sensor or flow monitor, measures the flow of blood drawn by blood pump 31. Blood flow detector 13 may transmit a feedback signal representing the blood flow to a controller 11. Citrate pump 19 supplements blood flow 20 with a flow 22 of citrate ion anticoagulant from citrate solution 17. Citrate solution 17 may contain a selected concentration of citric acid, trisodium citrate, and/or another source of citrate ions.

An optional anticoagulant, such as heparin, may be added upstream of hemofilter 39 using a heparin pump 33 to inject a flow 24 into blood flow 20. A pre-filter pressure sensor 35 measures pressure in blood flow 20 upstream of hemofilter 39. Pressure sensor 35 may transmit a signal representing pressure or flow to a controller 11. Also upstream of hemofilter 39, a pre-dilution pump 37 may further supplement the unfiltered blood flow 20 with a flow 26 from a source of substitution fluid 43. Particularly for HFHV therapies, a substitution fluid 43 may be necessary to maintain an adequate volume of blood plasma in the patient. Substitution fluid 43 may be any sterile intravenous fluid having a concentration of electrolytes similar to the plasma.

Hemofilter 39 transfers water and waste solutes out of the blood. During CRRT, hemofilter 39 performs the function of an artificial kidney or dialysis filter. The hemofilter 39 may be constructed with two flow paths separated from each other by a semi-permeable membrane. One flow path passes blood flow 20, while the second flow path 32 passes a dialysate, preferable in a direction opposite that of blood flow 20, to promote a diffusion gradient. As in conventional dialysis systems, the dialysate contains a concentration of solutes of lower concentration than what is found in the unfiltered blood flow 20. Through osmosis and/or differential pressure across the semi-permeable membrane, hemofilter 39 removes unwanted waste products from blood flow 20 for entrainment in dialysate flow path 32.

A filtration pump 49, which may be similar in construction to other pumps in the circuit, draws dialysate from hemofilter 39 into the dialysate flow path 32, which leads to a dialysate collector 51. A filtrate pressure sensor in flow path 32 may be installed for detection of dialysate flow rate, and transmission of a feedback signal representing dialysate flow rate to controller 11. Dialysate accumulating in collector 51 may be disposed of as a waste product.

The dialysate in flow path 32 may be routed through a blood leak detector 46, which may be set to alarm upon detection of excessive presence of blood plasma in dialysate flow path 32. One example of a blood leak detector 46 is a non-invasive optical sensor manufactured by Introtek Intl. of Edgewood, N.Y. The Introtek leak detector operates on the principle of light absorption. Dialysate flow is routed to the leak detector through clear plastic tubing, into which a beam of light is directed. The specific amount of light absorbed by the dialysate is compared to a calibrated pre-set threshold. If the threshold is exceeded due to the presence of too much blood leaking into flow path 32 through a perforation in the membrane of hemofilter 39, the optical leak detector may output an analog or digital alarm signal to indicate an out-of-tolerance condition. In one embodiment, controller 11 may receive this alarm, and in response, shut down blood pump 31, thereby interrupting the CRRT until hemofilter 39 can be replaced.

A flow 40 of filtered blood exits hemofilter 39 on the downstream side of the filter. An electrolyte sensor 15 may be installed in the exit flow 40 to sense various electrolyte levels and transmit signals representing those levels to a controller 11. A post-dilution flow 28 may supplement filtered blood flow 40 downstream of hemofilter 39. A post-dilution pump 53 draws flow 28 from a source of substitution fluid. In one embodiment, source 43 provides the source of substitution fluid for both pre-dilution pump 37 and post-dilution pump 53.

In the embodiment shown, pre-dilution flow 26 and post-dilution flow 28 originate from a common flow 30 of substitution fluid exiting source 43. A temperature sensor 55 and heater 57 may be installed in the flow paths of substitution fluid, preferably within the path of common flow 30, to control substitution fluid temperature. Temperature sensor 55 may transmit an analog or digital signal representing substitution fluid temperature to controller 11. In response to receiving a temperature signal, controller 11 may switch on or off heater 57, or otherwise adjust the output of heater 57, for example, by transmitting a control signal that varies the amount of electrical current energizing an electric heating element of heater 57. In this way, the temperature of filtered blood flow 40 may be maintained at an optimal level when delivered back to the patient.

A post-filter pressure sensor 41 may be placed into the path of blood flow 40 for making pressure and flow measurements downstream of hemofilter 39. Pressure sensor 41 may transmit a signal representing pressure or flow to a controller 11. An air bubble trap 61 may be placed into blood flow 40 for removal of unwanted micro bubbles.

An electrolyte source 63 may be provided for replenishing blood flow 40 with electrolytes such as bicarbonate, calcium, chloride, copper, glucose, iron, magnesium, manganese, phosphate, potassium, sodium, and zinc that may have been depleted through filtration. In one embodiment, electrolyte source 63 provides a solution containing calcium ions and magnesium ions, contained, for example, in a transfusion or infusion bag. An electrolyte pump 65, which may be similar in construction to other pumps in the circuit, draws the electrolyte solution from electrolyte source 63 into a flow 36 that supplements blood flow 40.

An air bubble detector 67 may be placed into blood flow 40 downstream of bubble trap 61, and preferably downstream of all pumps in the circuit, to detect the undesirable presence of air bubbles or air gaps in blood flow 40. Any air bubble detector known in the medical arts, such as those operating on ultrasonic or infrared sensing technology, may be used for this purpose. An automatic clamp 69 may be placed between air bubble detector 67 and patient blood return site 71. In one embodiment, a solenoid valve may be employed as automatic clamp 69. In another embodiment, air bubble detector 67 and automatic clamp 69 interface electronically with controller 11. In response to detecting passage of an air gap or air bubble, air bubble detector may transmit an alarm signal to controller 11. In response to receiving the alarm signal, controller 11 may output an actuation signal to automatic clamp 69, causing it to arrest the blood flow. In another embodiment, the same actuation signal may shut off blood pump 31.

Figure 3:
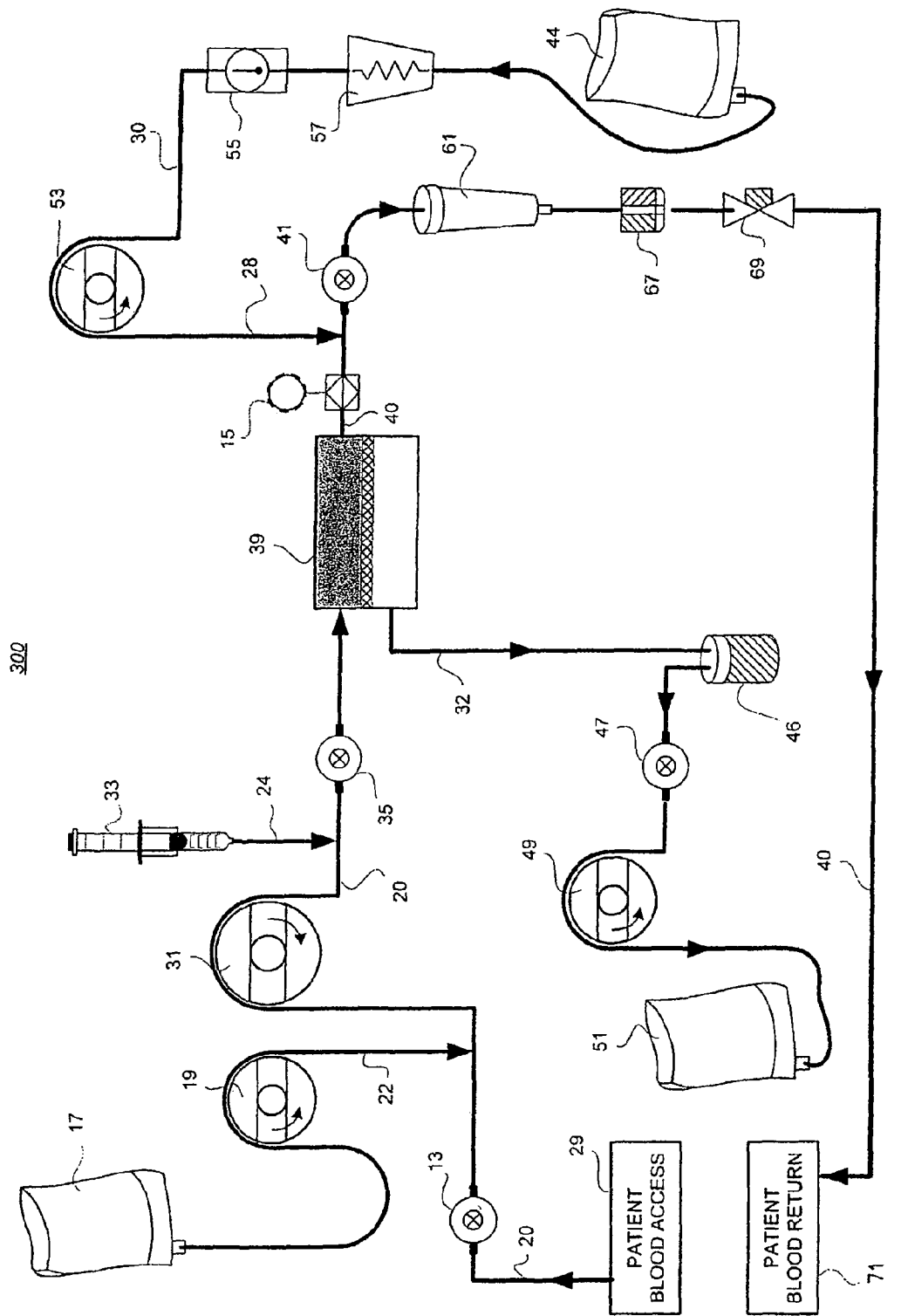
FIG. 3 is another diagram of a blood filtration circuit for CRRT treatment, configured to provide substitution solution and supplemental electrolytes from a common source.

FIG. 3 is another diagram of a blood filtration circuit for CRRT treatment that may be optimized for regional citrate anticoagulation according to an embodiment of the invention. This embodiment may be suitable for CVVH type therapy. System 300 shown in FIG. 3 may be configured to provide substitution solution and supplemental electrolytes from a common source.

System 300 operates similarly to system 200. However, in system 300, substitution fluid may be introduced only as post-dilution fluid, downstream of hemofilter 39, by post-dilution pump 53. No pre-dilution flow of substitution fluid is provided. System 300 may also be characterized by the absence of a separate electrolyte pump. Post-dilution pump 53 may provide both substitution fluid and supplemental electrolyte solution, thereby eliminating the need for the electrolyte pump. The supplemental electrolytes may be included within substitution fluid 44, or the electrolytes may be provided from a separate source coupled to pump 53. In one embodiment, the supplemental electrolytes are provided by a chloride-based solution that includes calcium and magnesium ions.

Figure 4:
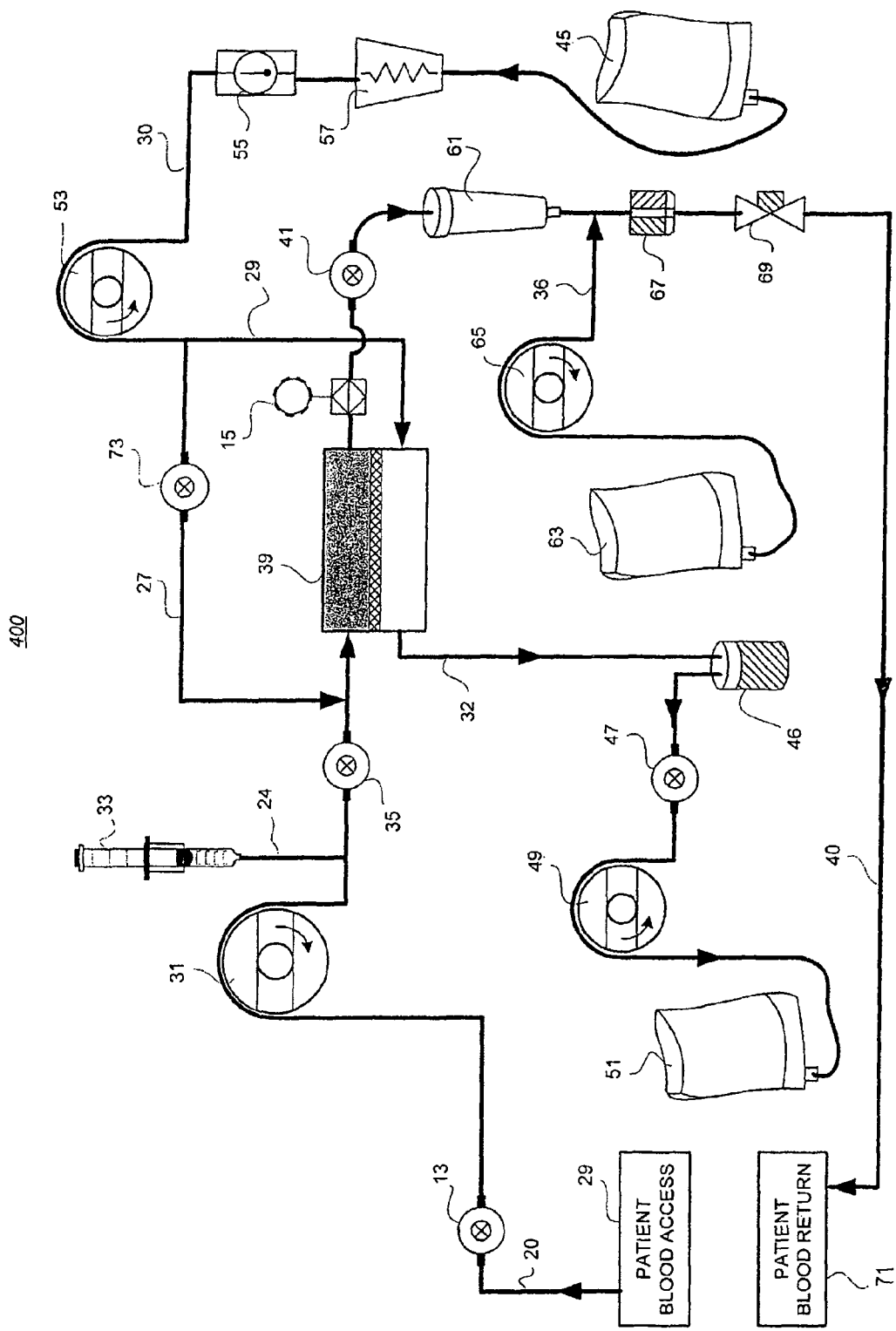
FIG. 4 is another diagram of a blood filtration circuit for CRRT treatment, configured to provide substitution solution and anticoagulant from a common source.

FIG. 4 illustrates another blood filtration circuit for optimizing CRRT using regional citrate anticoagulation according to an embodiment of the invention. In this embodiment, suitable for CVVH or CVVHD, system 400 is configured to provide substitution solution and citrate anticoagulant from a common source. The common source may be connected to provide a pre-dilution substitution fluid, or to provide a dialysate solution.

System 400 operates similarly to the blood filtration circuits previously described. In this circuit, a source of citrate ions is combined with, and provided from, a source of substitution fluid 45. Pump 53 may pump fluid 45 through one or both of two flow paths 27 and 29. Flow 27 provides a pre-dilution supplement with citrate anticoagulant to blood flow 20 entering hemofilter 39. Flow 29 provides a dialysate with citrate anticoagulant to dialysate flow path 32. In this fashion, a citrate anticoagulant may be applied along either surface of the hemofilter membrane, either as a pre-dilution substitution fluid, or as a dialysate. When provided as a pre-dilution substitution fluid, a sensor such as pressure sensor 73 may be used to detect flow 27, or flow, rate, or pressure in the pre-dilution line. Note also that citrate may be added through pump 53, thus system 400 may not require the separate citrate pump 19 or source of citrate solution 17, of system 200. In another embodiment, citrate may be added through a post-dilution substitution fluid.

Figure 5:
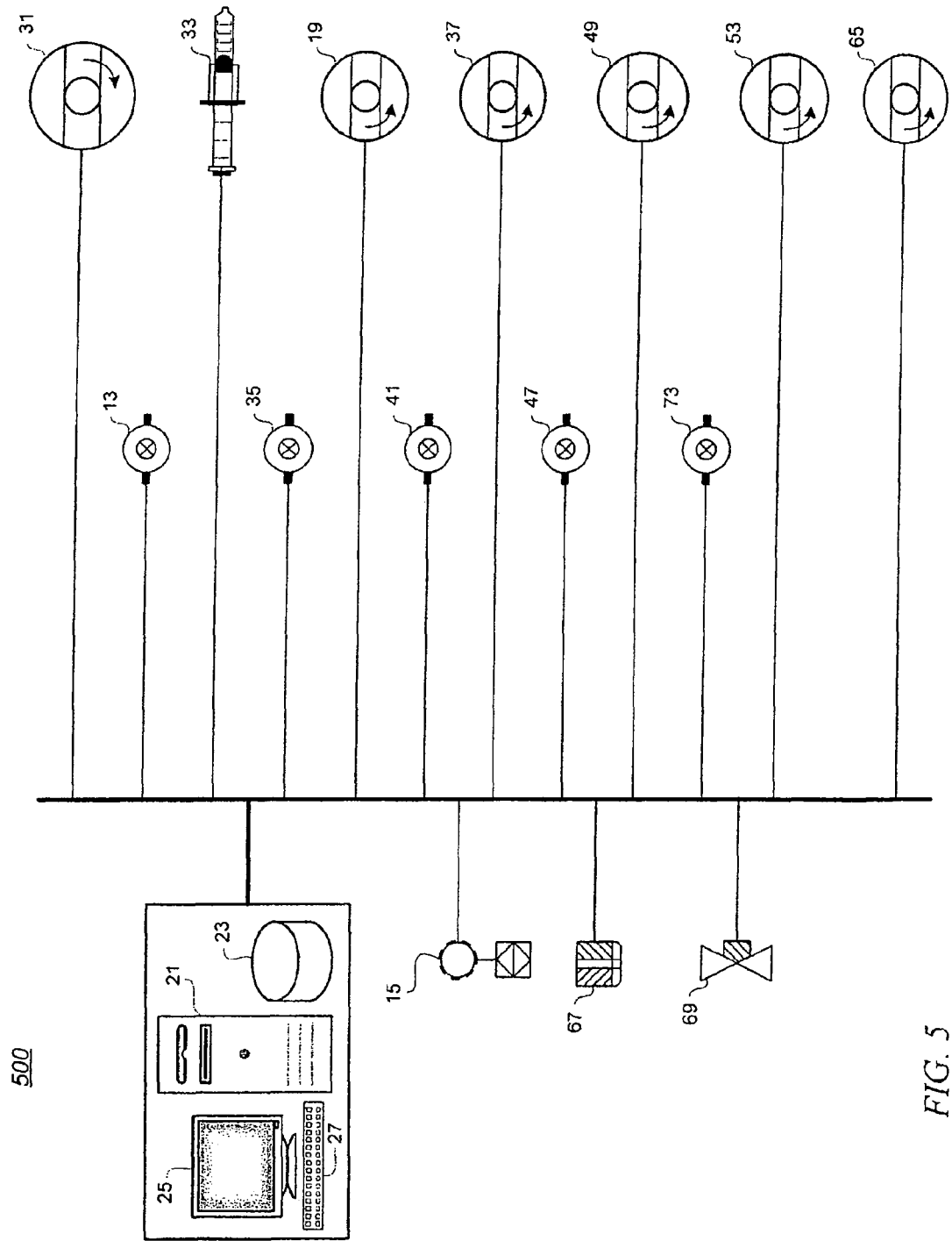
FIG. 5 shows an exemplary schematic diagram of a system according to the invention for controlling components shown in FIGS. 1-3.

FIG. 5 shows an exemplary schematic diagram of a system 500 according to another embodiment of the invention for controlling components shown in FIGS. 2-4. As in the embodiment of system 100, a controller 11 communicates to components within the blood filtration circuit via signal line 12. Through this communication link, instrumentation such as electrolyte sensor 15, blood leak detector 46, temperature sensor 55, air bubble detector 67, and pressure sensors 13, 35, 41, 47, and 73 may transmit signals representing sensed or detected system parameters for input to controller 11. In response to receiving input signals, controller 11 may automatically output control signals through signal line 12 for actuating components such as citrate pump 19, blood pump 31, heparin pump 33, pre-dilution pump 37, filtration pump 49, post-dilution pump 53, electrolyte pump 65, and the automatic clamp 69. For example, one or more of the pressure sensors may provide feedback representing a flow rate to controller 11 for input to a PID or state-space control algorithm. The form of control signals automatically output from controller 11 may be determined according to control algorithms stored in memory 23 and executed by CPU 21. Alternatively, CPU 21 may display calculated results on a display 25 for manual adjustment of system parameters via user interface 27. In another embodiment, data may be stored in memory 23 (e.g. as a lookup table) for use in calculating system control signals.

Figure 6:
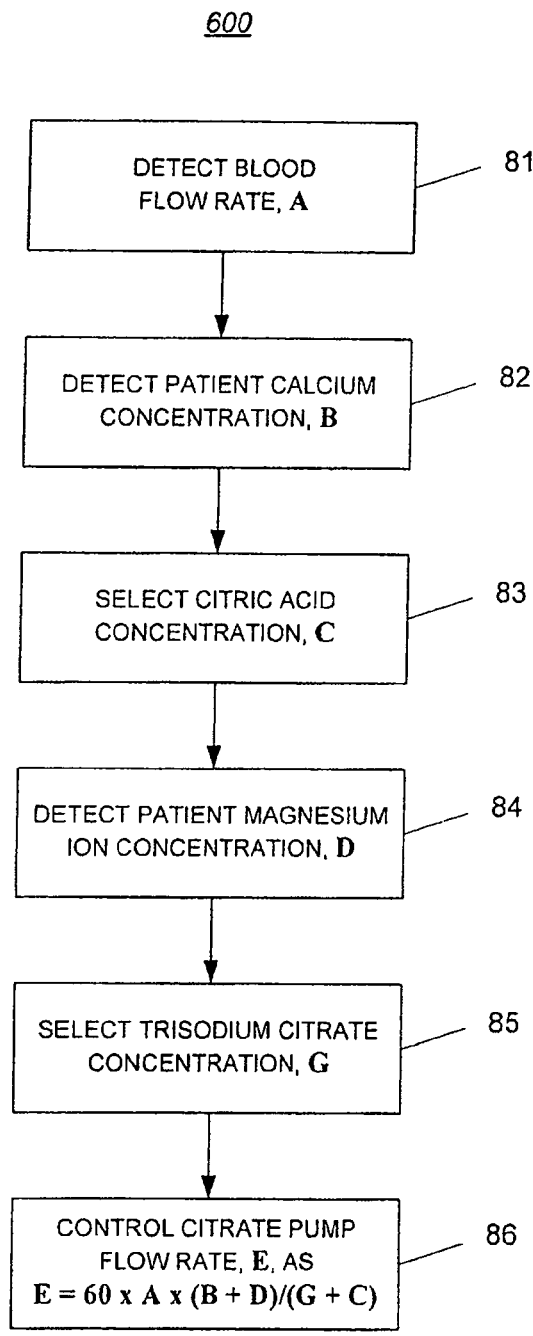
FIG. 6 is a flow chart showing a method according to the invention for controlling citrate pump flow rate during CRRT treatment using regional citrate anticoagulation.

FIG. 6 is a flow chart showing a method 600 according to an embodiment of the invention for controlling citrate pump flow rate during CRRT treatment using regional citrate anticoagulation. The steps of method 600 may be carried out either manually or automatically.

Method 600 begins with step 81. In this first step, a blood flow rate denoted A may be detected in a patient undergoing CRRT. A blood flow detector 13 may be used to perform this step. The blood flow detector may be operated manually by a health care worker, or automatically as an integral component of a system per the invention. The next step 82 is another detecting step, in which calcium concentration B is detected in a blood sample from the patient. Again, this step may be performed automatically by the system or manually by a worker using an electrolyte sensor suitable for the purpose.

In the next step 83, a citric acid concentration C may be selected for the therapy. The citric acid concentration may be selected for a pre-dilution substitution fluid, for a post-dilution substitution fluid, or for a dialysate solution. Next, in step 84, a concentration D of magnesium in a blood sample of the patient may be detected, manually or automatically, using an appropriate electrolyte sensor. The next step in the sequence is step 85, which is an optional step, depending on whether equation (1) or equation (2) is used in the final calculation of step 611. If equation (1) is used, step 85 may not be performed. If equation (2) is used, step 85 may be performed by selecting a trisodium citrate concentration G as an anticoagulant for supplementing blood flow in an extracorporeal filtration circuit. The trisodium citrate concentration G may be selected for a pre-dilution substitution fluid, for a post-dilution substitution fluid, or for a dialysate solution.

The final step of method 600 is step 86. In step 86 a calculation is performed for controlling citrate flow rate E, or equivalently, for controlling the flow rate E of a citrate pump, substitution pump, or dialysate pump, depending on which pump has been selected to provide a source of citrate ions. If optional step 85 has not been performed, step 86 controls citrate flow rate according to equation (1). If optional step 85 has been performed, step 86 controls citrate flow rate according to equation (2), as shown in FIG. 6. In either case, step 86 may be performed automatically using a controller such as controller 11. In this case, controller 11 would perform step 86 in response to receiving input signals for the parameters A, B, C, D, and G corresponding to the preceding steps of the method.

Alternatively, one or more steps of method 600 may also represent manual input of a system parameter into a formula for calculating citrate flow rate. For example, each step may be performed manually, using appropriate instrumentation. Then at step 86, a user inputs the results of all preceding steps into a controller. A user interface may be used for this purpose. In response to the inputs, the controller may automatically adjust citrate pump flow rate using an appropriate calculation. It should be appreciated that steps 81 to 85 of method 600 need not be performed in the sequence illustrated. Any sequence, or simultaneous performance of these steps, may produce a desired result in the final step 86.

Figure 7:
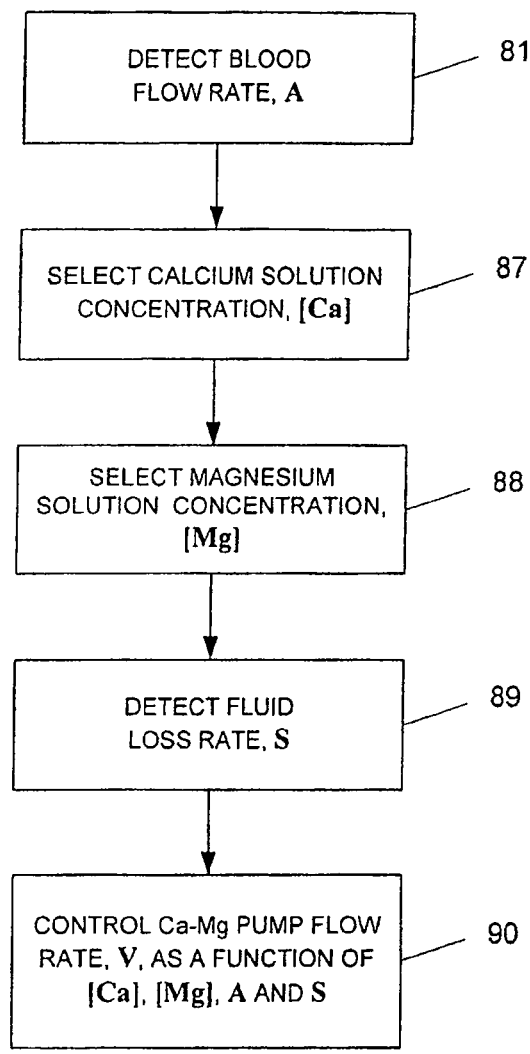
FIG. 7 is a flow chart showing a method according to the invention for controlling electrolyte pump flow rate during CRRT treatment using regional citrate anticoagulation.

FIG. 7 is a flow chart showing a method 700 according to an embodiment of the invention for controlling electrolyte pump flow rate during CRRT treatment using regional citrate anticoagulation. Method 700 may be performed in conjunction with method 600. In method 700, an electrolyte pump (e.g. pump 65) may provide calcium ions and magnesium ions to replenish these electrolytes that are lost in the filtration process.

Method 700 begins at step 87, in which a calcium ion concentration [Ca] may be selected for an electrolyte solution. Similarly, in step 88, a magnesium ion concentration [Mg] may be selected for an electrolyte solution. In one embodiment, [Ca] and [Mg] are selected for a common chloride based solution.

In the next step 81, a blood flow rate, A, may be detected for a patient undergoing CRRT. In one embodiment, this step may be identical to step 81 of method 600. Another detection step may be performed in step 89. In step 89, a fluid loss rate, S, may be detected by measuring the rate of plasma migration across the semi-permeable membrane of an artificial kidney in service during CRRT. Fluid loss rate S may be detected by volumetric measurement of the plasma over time, or by an appropriate flow or pressure sensor (such as sensor 47) placed in an outflow line of the hemofilter (i.e. flow path 32). In one example where dialysate flow is present, subtracting a known dialysate flow rate from the hemofilter outflow rate will yield a value for S. One or more of steps 81, 87, 88, and 89 may be data collection or data input steps, and may be performed simultaneously, or in any desired sequence.

The final step in method 700 is step 90, which may be a calculation and control step. In this step, a calculation may be performed for controlling the electrolyte pump flow rate V. In one embodiment, step 90 calculates V as a function of [Ca], [Mg], A, and S. The result of this calculation may be automatically or manually transmitted as an input control signal to the electrolyte pump to control the introduction of electrolytes into the blood flow after filtration.

Figure 8:
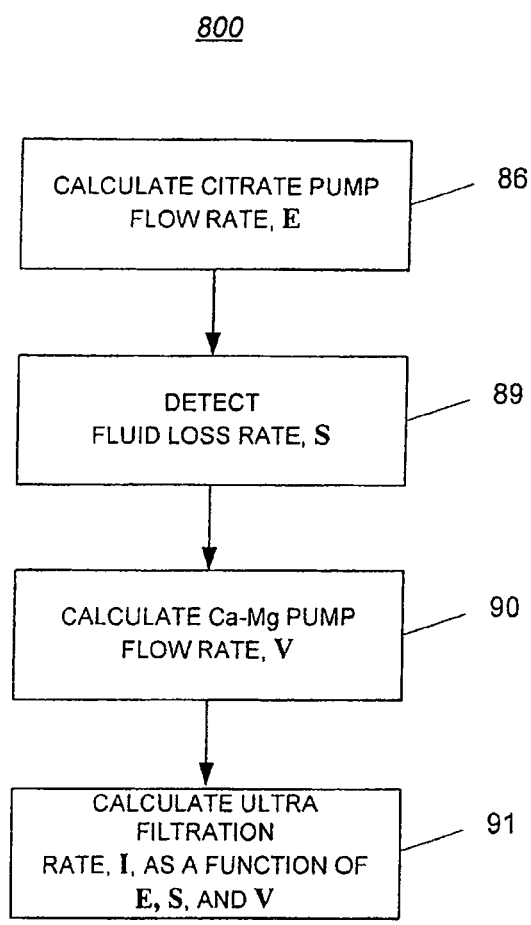
FIG. 8 is a flow chart showing a method according to the invention for calculating ultrafiltration rate during CRRT treatment using regional citrate anticoagulation.

FIG. 8 is a flow chart showing a method 800 according to another embodiment of the invention for calculating ultrafiltration rate during CRRT treatment using regional citrate anticoagulation. Method 800 may be used in conjunction with methods 600 and 700 for controlling the overall CRRT process.

Method 800 may contain three steps for acquiring input data for its final calculation. The first of these steps is step 86, for calculating a citrate pump flow rate E. This step may be performed identically as in step 86 of method 600. The second step is step 89, which may be a detection step for detecting fluid loss rate S. This step may be performed identically as in step 89 of method 700. The third step is step 90, for calculating an electrolyte pump flow rate V. Step 90 may be performed identically as in step 90 of method 700. Once the input data has been acquired from these three steps, simultaneously or in any sequential order, a final calculation step 91 may be executed. In step 91, an ultrafiltration rate I may be calculated as a function of E, S, and V.

Figure 9:
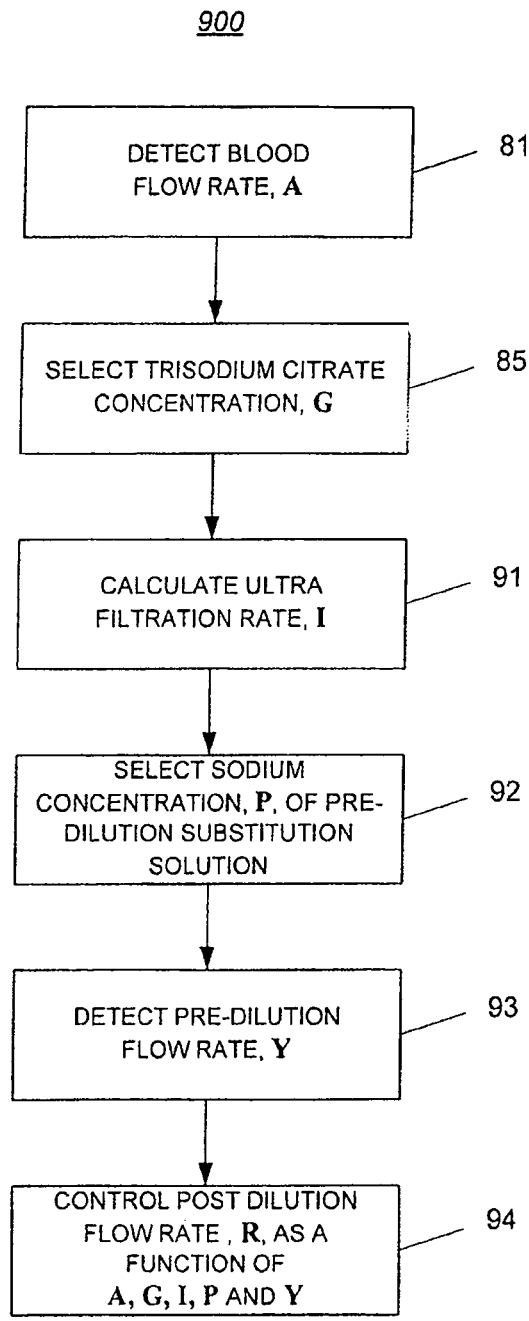
FIG. 9 is a flow chart showing a method according to the invention for controlling post dilution flow rate during CRRT treatment using regional citrate anticoagulation.

FIG. 9 is a flow chart showing a method 900 according to an embodiment of the invention for controlling post dilution flow rate during CRRT treatment using regional citrate anticoagulation. Method 900 may also be used in conjunction with methods previously disclosed for comprehensive control of a CRRT system according to the invention.

The first three steps illustrated in the flow chart of FIG. 9 may be performed identically or in a similar manner to previously described steps. Step 81 may be performed as in method 600 to detect a blood flow rate A. Step 85 may be performed as in method 600 to select a trisodium citrate concentration G. Step 91 may be performed as in method 800 to calculate an ultrafiltration rate I.

In the next step 92, a sodium concentration, P, may be selected for a pre-dilution substitution solution used for supplementing the blood flow in the extracorporeal circuit. For example, step 92 may include specifying an appropriate sodium concentration for substitution fluid source 43 in system 200. The next step, 93, may be a detection step for detecting a pre-dilution fluid flow rate, Y. A flow sensor, a pressure sensor (e.g. sensor 73), or combination of pressure sensors may be placed in the flow path of the pre-dilution fluid or elsewhere in the circuit to detect this flow rate.

The final step of method 900 is step 94. The steps preceding step 94 may be performed simultaneously or in any convenient sequence. In step 94, a calculation may be performed using the results of the preceding process steps as inputs to arrive at an output value for controlling the flow rate, R, of the post-dilution substitution fluid. That is, R may be calculated as a function of A, G, I, P and Y. In one embodiment, this calculation may be performed automatically to control the output flow rate delivered by a post dilution pump 53.

Figure 10:
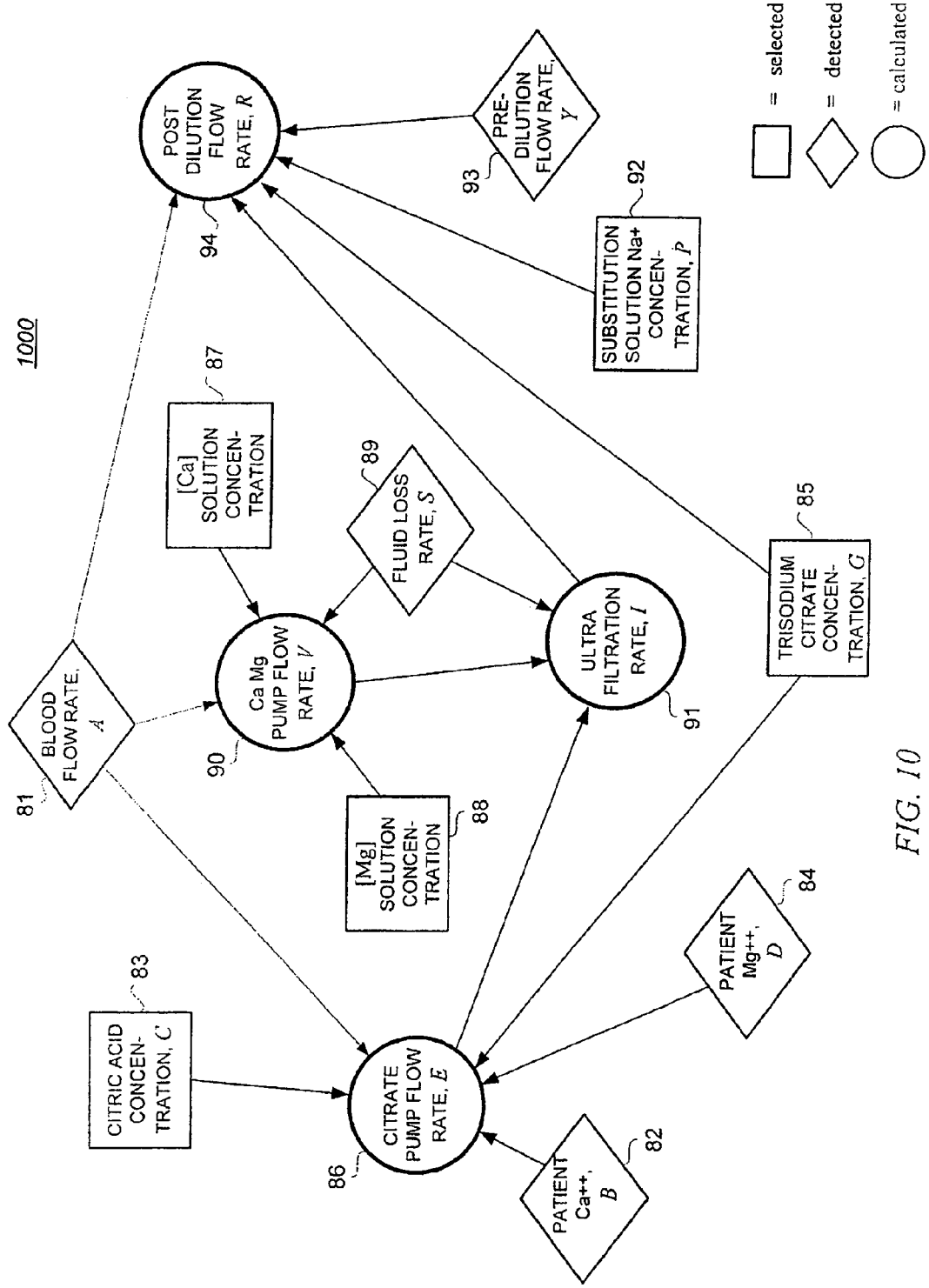
FIG. 10 is a flow chart illustrating the interdependency of input and output parameters, derived from components of a blood filtration circuit, for automating and optimizing CRRT treatment according to the invention.

FIG. 10 is a flow chart of an embodiment of a method according to the invention that illustrates the interdependency of the various input and output parameters described in all of the foregoing methods. In this chart, method 1000 combines methods 600, 700, 800, and 900 into a single method for deriving output parameters, from components of a blood filtration circuit, for automating and optimizing CRRT treatment using regional citrate anticoagulation according to the invention.

There are three types of process blocks illustrated in the chart of FIG. 10. A rectangular block denotes a selection step, wherein a process input parameter such as a chemical concentration may be selected. A diamond shaped block denotes a detection step, wherein a process input parameter such as a flow rate may be detected. A circular block denotes a calculation step, which may produce a process input parameter or a process output parameter. Arrows originate from process input steps and terminate at process output steps. Each of the calculation steps shown in the chart provides a flow rate, and all flow rates are interdependent in order to optimize system operation.

Thus, according to the invention, citrate pump flow rate E may be a function of blood flow rate A, patient calcium concentration B, citric acid concentration C, patient magnesium ion concentration D, and trisodium citrate concentration G.

Electrolyte pump flow rate V may be a function of blood flow rate A, calcium solution concentration [Ca], magnesium solution concentration [Mg], and fluid loss rate S.

Ultrafiltration rate I may be a function of citrate pump flow rate E, fluid loss rate S, and electrolyte pump flow rate V.

And, post-dilution pump flow rate R may be a function of blood flow rate A, trisodium citrate concentration G, ultrafiltration rate I, pre-dilution substitution solution sodium concentration P, and pre-dilution flow rate Y.

The following sections provide additional disclosure of algorithms that may be used to optimize CRRT therapies according to various embodiments of the present invention. One or more of the algorithms may use codes that are listed in Table 1 below. The table includes a description of the parameter and definition of the parameter represented by each code. The table also indicates in the right-most column whether the parameter is selected, detected, or calculated. Dimensional units such as (ml/min) are provided for illustrative purposes only.

TABLE 1

| CODE | PARAMETER | DEFINITION | TYPE |
|---|---|---|---|
| A | blood flow rate (ml/min) | range: 30 to 450 ml/min | detected |
| A' | plasma flow rate (ml/min) | depends on A and hematocrit: $A' = A \times (1 - Hct)$ | calculated |
| B | Pca (mmol/l) | patient plasma concentration of calcium (0.8 to 1.6 mmol/l) | detected |
| C | Ctcitrate (mmol) | concentration of citrate | selected |
| D | Pmg | patient plasma concentration of Magnesium (0.55 to 1.15 mmol/l) | detected |
| E | citrate flow rate (ml/h) | citrate flow rate needed to chelate all Ca and Mg ions from patient plasma | calculated |

TABLE 1-continued

| CODE | PARAMETER | DEFINITION | TYPE |
|---|---|---|---|
| F | Pna (mmol/l) | patient plasma concentration of Na (125 to 155 mmol/l) | detected |
| G | Nacitrate (mmol/l) | sodium concentration in citrate solution | selected |
| H | Na in (mmol/h) | no. of mmol of Na entering hemofilter per hour | calculated |
| I | UF rate (ml/h) | filtration amount not returned to patient | calculated |
| J | blood flow rate out (ml/min) | blood flow rate just after hemofilter | calculated |
| K | Na filtered (mmol/h) | no. of Na molecules filtrated per hour | calculated |
| L | Na out (mmol/h) | no. of plasma Na molecules exiting the Hemofilter per hour | calculated |
| M | Na+ sieving coefficient | sieving coefficient of Na thru hemofilter | selected |
| M' | trisodium citrate sieving coefficient | sieving coefficient of trisodium citrate thru the hemofilter | selected |
| N | filtration flow rate (ml/h) | total filtration volume thru hemofilter | calculated |
| O | Na in (mmol/l) | plasma concentration of Na just before the hemofilter | calculated |
| P | Na pre-dilution (mmol/l) | Na concentration of pre-dilution substitution solution | selected |
| P' | Na post-dilution | Na concentration of post-dilution substitution solution | selected |
| R | substitution flow rate | post-dilution substitution flow rate | calculated |
| S | fluid loss rate (ml/h) | desired fluid loss rate for the patient, per hour (0 to 2000 ml/h) | detected |
| T | Cacitrate sieving coefficient | sieving coefficient of calcium citrate thru the hemofilter | selected |
| T' | calcium sieving coefficient | sieving coefficient of calcium thru the hemofilter | selected |
| U | Ca solution concentration (mmol/l) | concentration of calcium in chloride Ca/Mg solution | selected |
| V | Ca/Mg flow rate (ml/h) | flow rate of chloride Ca/Mg solution | calculated |
| W | Ca citrate in (mmol/h) | no. of plasma calcium-citrate molecules entering the hemofilter | calculated |
| X | filtration fraction | filtration fraction thru the hemofilter | calculated |
| Y | pre-dilution flow rate (ml/h) | flow rate of pre-dilution substitution fluid | detected |
| Z | total fluid loss (ml) | total fluid loss expected for the patient | detected |
| AA | Na inside Ca/Mg | concentration of sodium inside Ca/Mg complementary solution | selected |
| AB | protidemia (g/L) | total weight of proteins in 1 L of plasma Before hemofilter | calculated |
| AC | MgCitrate sieving Coefficient | sieving coefficient of MagnesiumCitrate molecules thru the hemofilter | selected |
| AD | bicarbonate sieving coefficient | sieving coefficient of bicarbonate ions (HCO3−) | selected |
| AE | Pbicar (mmol/L) | patient plasma concentration of bicarbonate (mmol/l) | detected |
| AF | citric acid sieving coefficient | sieving coefficient of citric acid coming from citrate solution | selected |
| AG | Ca++ post concentration | Ca++ concentration of post-dilution substitution solution | selected |

Citrate Flow Rate

Automatic regulation of citrate flow rate during CRRT in any of the systems herein described may be implemented according to the rules provided in the following Table 2:

TABLE 2

| CONDITION | ADJUSTMENT |
|---|---|
| AG > 0.5 mmol/L | increase E by 2.5 mmol/h |
| 0.4 < AG < 0.5 mmol/L | increase E by 1.5 mmol/h |
| 0.2 < AG < 0.4 mmol/L | no change |
| AG < 0.2 mmol/L | decrease E by 1.5 mmol/h |
| 7.45 < plasma pH < 7.55 | increase E by 1.5 mmol/h |
| plasma pH > 7.55 | increase E by 2.5 mmol/h |
| increase in plasma total calcium | adjust E per equation (1) or (2) |
| decrease in plasma total calcium | adjust E per equation (1) or (2) |
| increase in plasma total magnesium | adjust E per equation (1) or (2) |
| decrease in plasma total magnesium | adjust E per equation (1) or (2) |
| increase in A | adjust E per equation (1) or (2) |
| decrease in A | adjust E per equation (1) or (2) |

Each of the rules described in the above table may be implemented manually under by a health care worker by manipulating instruments directly, or through a user interface to a controller described, for example, in system 100 or system 500. The same rules may be implemented automatically by a controller executing an adjustment algorithm stored as a series of instructions or software in memory executable by the controller CPU.

Filtration Flow Rate, N

The total filtration flow rate N may be calculated by accounting for the presence of sodium in the circuit. The amount of sodium after addition of the post-dilution substitution solution equals the amount of sodium entering the hemofilter, plus the amount of sodium introduced by the post-dilution substitution solution, minus the amount of sodium lost through the hemofilter. This may be expressed algebraically as:

$$N=\{[(F\times60\times A'-S)-(V\times AA)]-H\times1000+P'\times(Y+E+V+S)\}/\{[P-(M\times H/(60\times A'+E+Y))]\times1000\times1000/(1000-AB)\} \quad (3)$$

or as:

$$N=\{[(F\times60\times A'-S)-(V\times AA)]-H\times1000+P'\times(Y+E+V+S)\}/\{[P'-1000\times1000/(1000-AB)]\times[M\times(H-3\times H')+M'\times3\times H']/(60\times A'+E+Y)\} \quad (4)$$

where H' represents the number of excess trisodiumcitrate molecules circulating per hour through the hemofilter. H' may be given by:

$$H'=[C\times E)/1000-(B+D)\times60\times A'/1000]\times(G/3)/C \quad (5)$$

Post-Dilution Flow Rate, R

The filtration flow rate N is the sum of the post-dilution flow rate R, the pre-dilution flow rate Y, the citrate solution flow rate E, the Ca/Mg solution flow rate V, and the fluid loss rate S. Therefore, the post-dilution substitution fluid flow rate, R, may be calculated according to:

$$R=N-(E+S+V+Y) \quad (6)$$

Calcium/Magnesium Pump Flow Rate, V

A method according to the invention for calculating an optimal Ca/Mg pump flow rate V may be based on an assumption that the total calcium concentration of blood entering the extracorporeal circuit is equivalent to the total calcium concentration returning to the patient at the exit of the circuit in order to maintain a stable calcemia. Thus, the calcium returning to the patient may be equivalent to the calcium content before the hemofilter, plus the calcium contribution from the post-dilution substitution solution, plus the calcium contribution from the Ca/Mg electrolyte solution, minus the calcium lost through the hemofilter.

Two situations may occur that affect the algorithm chosen for calculating V. The first situation occurs when trisodium citrate molecules introduced into the blood flow are not sufficient to chelate all calcium and magnesium from the blood circulating upstream of the hemofilter. In this case, the Ca/Mg pump flow rate V may be calculated as:

$$V=[B\times(60\times A'-S)/1000-W+(\alpha\times\beta)/\gamma]\times\gamma/(AA-P')\times\beta+(U/1000)\times\gamma$$

where $\alpha=[F\times(60\times A'-S)-H\times1000+P'\times(Y+E+S)]$;

$\beta=1000\times[T\times((E\times C/1000)\times(B/(B+D))]+T\times(1/2)[W-(E\times C/1000)\times(B/(B+D))]$;

and $$\gamma=P'\times(60\times A'+E+Y)\times(1000-AB)-M\times H\times1000\times1000 \quad (7)$$

In this first situation, it may be of interest to calculate the number of calcium molecules filtrated through the hemofilter. The number of calcium molecules filtrated per hour, denoted as "Cafiltrated_1", may be calculated as:

$$\text{Cafiltrated}\_1=[\alpha-(V\times AA)]\times\beta/\gamma \quad (8)$$

In the second situation, the trisodium citrate molecules are sufficient to chelate all calcium and magnesium from the blood circulating upstream of the hemofilter. In this case, the Ca/Mg pump flow rate V may be calculated as:

$$V=[B\times(60\times A'-S)/1000-W+(\delta/\epsilon)\times\epsilon/[1000\times T\times W\times V\times(AA-P')+U/1000\times\epsilon]$$

where $\delta=1000\times T\times W\times(F\times(60\times A'-S)-H\times1000+P'\times(Y+E+S))$; and $$\epsilon=P'\times(60\times A'+E+Y)\times(1000-AB)-1000\times1000\times(M\times(H-3\times H')+M'\times3\times H') \quad (9)$$

In this second situation, the number of calcium molecules filtrated per hour, denoted as "Cafiltrated_2", may be calculated as:

$$\text{Cafiltrated}\_2=1000\times T\times W\times(F\times(60\times A'-S)-(V\times AA)-H\times1000+P'\times(Y+E+V+S))/(60\times A'+E+Y)\times(1000-AB)\times(P'-1000\times(1000/(1000-AB))\times(M\times(H-3\times H')+M'\times3\times H')/(60\times A'+E+Y)) \quad (10)$$

Equations (8) and (10) may also be used to calculate the number of magnesium molecules filtrated through the hemofilter, by simply replacing the parameter B with D.

Bicarbonates Filtrated

Bicarbonate concentration in blood plasma during CRRT using regional citrate anticoagulation may also be of concern. Citrate added to the extracorporeal circuit through citrate anticoagulant solution (citric acid and trisodium citrate) will be converted later by the liver and muscles of the patient into bicarbonate according to the tri-carboxycilique cycle from the Krebs cycle. The present invention may also account for citrate converted into bicarbonate in this manner, by monitoring eventual bicarbonate concentration in the blood plasma returned to the patient. The invention may account for bicarbonate molecules under two different cases.

In the first case, the amount of bicarbonate molecules, BICout_1, may be calculated where the number of citrate molecules introduced by the citrate solution is equal to or less than the sum of total calcium and total magnesium present in the blood plasma. In this case, the following equation may be used:

$$\text{BICout}\_1=N\times[AD\times AE\times60\times A'+T\times E\times C\times B+AC\times E\times C\times DJ/[1000\times(B+D)\times(1000-AB)\times(60\times A'+E+Y)] \quad (11)$$

In the second case, the amount of bicarbonate molecules, BICout_2, may be calculated where the number of citrate molecules introduced by the citrate solution is greater than the sum of total calcium and total magnesium present in the blood plasma. In this case, the following equation may be used:

$$\text{BICout}\_2=N\times[AD\times AE\times60\times A'+M'\times E\times G/3-M'\times(B+D)\times60\times A'\times(G/3)/C+AF\times E\times(C-G/3)-AF\times(B+D)\times60\times A'\times(C-G/3)/C+T\times B\times60\times A'+AC\times D\times60\times A'J/[1000\times(1000-AB)\times(60\times A'+E+Y)] \quad (12)$$

Proofs for equations (1) through (12) are provided in U.S. Provisional Application 60/719,718.

Treatment Control

An embodiment of a system or method according to the invention may evaluate the composition of plasma circuit with regard to each electrolyte in the CRRT circuit in a step-by-step manner. The following tables provide formulas that may be used progressively to accurately calculate the number of molecules or concentration of any electrolyte of interest under various conditions and at various points in the circuit. The formulas shown in the tables may be stored as algorithms in a memory 23 as software executable by a CPU 21. The results of the calculations may be used in many ways. For example, the results may stored in memory 23, used as input in other algorithms, or displayed to a user via display unit 25.

Table 3 provides formulas for calculating the number of molecules of each electrolyte circulating per hour in the extracorporeal circuit.

Table 4 provides formulas for calculating the number of molecules of each electrolyte circulating per hour after citrate addition.

Table 5 provides formulas for calculating the number of molecules of each electrolyte circulating per hour after the addition of pre-dilution substitution solution.

Table 6 provides formulas for calculating the number of molecules of each electrolyte filtrated through the hemofilter per hour.

Table 7 provides formulas that may be used to calculate the number of molecules per hour for any particular electrolyte passing downstream of the hemofilter.

Table 8 provides formulas that may be used to calculate the number of molecules of each electrolyte circulating per hour after the addition of post-dilution substitution solution.

Table 9 provides formulas for calculating the number of molecules of each electrolyte returning to the patient.

Table 10 provides formulas for calculating the plasma concentration of each electrolyte returning to the patient.

TABLE 3

| ELECTROLYTE | PATIENT PLASMA CONCENTRATION (mmol/L) | NO. OF MOLECULES PER HOUR (mmol/h) |
|---|---|---|
| total calcium | TCA | $60 \times A' \times TCA/1000$ |
| total magnesium | TMG | $60 \times A' \times TMG/1000$ |
| sodium | NA | $60 \times A' \times NA/1000$ |
| potassium | K | $60 \times A' \times K/1000$ |
| glucose | GLU | $60 \times A' \times GLU/1000$ |
| bicarbonates | BIC | $60 \times A' \times BIC/1000$ |
| phosphate | PH | $60 \times A' \times PH/1000$ |
| chlorides | CL | $60 \times A' \times CL/1000$ |

In Table 4, the concentration of a particular electrolyte in citrate solution is denoted by an abbreviation for the electrolyte preceding the term "citrate". For example, "Na_citrate" denotes the concentration of sodium in citrate solution.

TABLE 4

| ELECTROLYTE | NO. OF MOLECULES PER HOUR AFTER CITRATE (mmol/h) |
|---|---|
| total calcium | $60 \times A' \times TCA/1000$ |
| total magnesium | $60 \times A' \times TMG/1000$ |
| sodium | $60 \times A' \times NA/1000 + E \times Na\_citrate/1000$ |
| potassium | $60 \times A' \times K/1000 + E \times K\_citrate/1000$ |
| glucose | $60 \times A' \times GLU/1000 + E \times Glu\_citrate/1000$ |
| bicarbonates | $60 \times A' \times BIC/1000 + E \times Bic\_citrate/1000$ |
| phosphate | $60 \times A' \times PH/1000 + E \times Pho\_citrate/1000$ |
| chlorides | $60 \times A' \times CL/1000 + E \times Cl\_citrate/1000$ |

In Table 5, the concentration of a particular electrolyte in pre-dilution substitution solution is denoted by an abbreviation for the electrolyte preceding the term "pre". For example, "Ca_pre" denotes the concentration of calcium in pre-dilution substitution solution.

TABLE 5

| ELECTROLYTE | NO. OF MOLECULES PER HOUR AFTER PRE-DILUTION SUB. SOLN. (mmol/h) |
|---|---|
| total calcium (CAin) | $60 \times A' \times TCA/1000 + Y \times Ca\_pre/1000$ |
| total magnesium (MGin) | $60 \times A' \times TMG/1000 + Y \times Mg\_pre/1000$ |
| sodium (NAin) | $60 \times A' \times NA/1000 + E \times Na\_citrate/1000 + Y \times P/1000$ |
| potassium (Kin) | $60 \times A' \times K/1000 + E \times K\_citrate/1000 + Y \times K\_pre/1000$ |
| glucose (GLUin) | $60 \times A' \times GLU/1000 + E \times Glu\_citrate/1000 + Y \times Glu\_pre/1000$ |
| bicarbonates (BICin) | $60 \times A' \times BIC/1000 + E \times Bic\_citrate/1000 + Y \times Bic\_pre/1000$ |
| phosphate (PHin) | $60 \times A' \times PH/1000 + E \times Pho\_citrate/1000 + Y \times Pho\_pre/1000$ |
| chlorides (CLin) | $60 \times A' \times CL/1000 + E \times Cl\_citrate/1000 + Y \times Cl\_pre/1000$ |

In Table 6, the sieving coefficient for a particular electrolyte is denoted by the term "Sie" preceding an abbreviation for the electrolyte. For example, "Sie_K" denotes the sieving coefficient for potassium.

TABLE 6

| ELECTROLYTE | NO. OF MOLECULES PER HOUR FILTRATED THROUGH HEMOFILTER (mmol/h) |
|---|---|
| total calcium (CAout) | per equation (8) or equation (10) |
| total magnesium (MGout) | per eq. (8) or eq. (10) by replacing B with D |
| sodium (NAout) | per eq. (3) or eq. (4) |
| potassium (Kout) | $(1000/(1000 - AB)) \times Sie\_K \times N/(60 \times A' + E + Y)$ |
| glucose (GLUout) | $(1000/(1000 - AB)) \times Sie\_Glu \times N/(60 \times A' + E + Y)$ |
| bicarbonates (BICout) | per eq. (11) or eq. (12) |
| phosphate (PHout) | $(1000/(1000 - AB)) \times Sie\_Pho \times N/(60 \times A' + E + Y)$ |
| chlorides (CLout) | $(1000/(1000 - AB)) \times Sie\_Cl \times N/(60 \times A' + E + Y)$ |

TABLE 7

| ELECTROLYTE | NO. OF MOLECULES PER HOUR AFTER HEMOFILTER (mmol/h) |
|---|---|
| total calcium | CAin − CAout |
| total magnesium | MGin − MGout |
| sodium | NAin − NAout |
| potassium | Kin − Kout |
| glucose | GLUin − GLUout |
| bicarbonates | BICin − BICout |
| phosphate | PHin − PHout |
| chlorides | CLin − CLout |

In Table 8, the post-dilution substitution solution concentration for a particular electrolyte is denoted by an abbreviation for the electrolyte preceding the term "post". For example, "K_post" denotes the concentration of potassium in the post-dilution substitution solution.

TABLE 8

| ELECTROLYTE | NO. OF MOLECULES PER HOUR AFTER post DILUTION SUB. SOLN. (mmol/h) |
|---|---|
| total calcium | CAin − Caout + Ca_post × R/1000 |
| total magnesium | MGin − Mgout + Mg_post × R/1000 |
| sodium | NAin − Naout + Na_post × R/1000 |
| potassium | Kin − Kout + K_post × R/1000 |
| glucose | GLUin − GLUout + Glu_post × R/1000 |
| bicarbonates | BICin − BICout + Bic_post × R/1000 |
| phosphate | PHin − PHout + Pho_post × R/1000 |
| chlorides | CLin − CLout + Cl_post × R/1000 |

In Table 9, the Ca/Mg complementation solution concentration for a particular electrolyte is denoted by an abbreviation for the electrolyte preceding the term "Cp". For example, "Bic_Cp" denotes the CaMg complementation solution concentration of bicarbonate.

TABLE 9

| ELECTROLYTE | NO. OF MOLECULES PER HOUR AT PATIENT RETURN (mmol/h) |
|---|---|
| total calcium (CAreturn) | CAin − CAout + Ca_post × R/1000 + Ca_Cp × V/1000 |

TABLE 9-continued

| ELECTROLYTE | NO. OF MOLECULES PER HOUR AT PATIENT RETURN (mmol/h) |
|---|---|
| total magnesium (MGreturn) | MGin − MGout + Mg_post × R/1000 + Mg_Cp × V/1000 |
| sodium (NAreturn) | NAin − NAout + Na_post × R/1000 + Na_Cp × V/1000 |
| potassium (Kreturn) | Kin − Kout + K_post × R/1000 + K_Cp × V/1000 |
| glucose (GLUreturn) | GLUin − GLUout + Glu_post × R/1000 + Glu_Cp × V/1000 |
| bicarbonates (BICreturn) | BICin − BICout + Bic_post × R/1000 + Bic_Cp × V/1000 |
| phosphate (PHreturn) | PHin − PHout + Pho_post × R/1000 + Pho_Cp × V/1000 |
| chlorides (CLreturn) | CLin − CLout + Cl_post × R/1000 + Cl_Cp × V/1000 |

TABLE 10

| ELECTROLYTE | PLASMA CONCENTRATION AT PATIENT RETURN (ml/min) |
|---|---|
| total calcium | 1000 × CAreturn/(60 × A' − S) |
| total magnesium | 1000 × MGreturn/(60 × A' − S) |
| sodium | 1000 × NAreturn/(60 × A' − S) |
| potassium | 1000 × Kreturn/(60 × A' − S) |
| glucose | 1000 × GLUreturn/(60 × A' − S) |
| bicarbonates | 1000 × BICreturn/(60 × A' − S) |
| phosphate | 1000 × PHreturn/(60 × A' − S) |
| chlorides | 1000 × CLreturn/(60 × A' − S) |

Conclusion

Prior methodologies cited in the background section provide insufficient guidance for controlling citrate flow into the bloodstream during CRRT. At a blood flow rate of 200 ml/min, the recommendation for citrate flow among these sources varies from 28 to 52.5 mmol/h, with a mean value of 36.6 mmol/h. However, applying a method according to the present invention to each of the systems in the cited literature, a mean value of 39.6 mmol/h citrate flow was achieved for a 200 ml/min blood flow rate. This mean value was achieved with minimal variance of 0.005 (see U.S. Provisional Application 60/719,718). Thus, the present invention provides consistent results regardless of the type of CRRT, and regardless of the blood flow rate chosen.

A further advantage provided by the invention is that it works equally well regardless of where citrate enters the circuit. Citrate may enter as a pre-dilution solution, as part of a pre-dilution substitution solution, or as part of a dialysate. Another advantage is that the invention may control the instantaneous blood flow rate, and also automatically adjust the citrate flow rate whenever blood flow rate changes. Another advantage is that the invention ensures that the plasma concentration of vital electrolytes returns to the patient at safe levels, e.g. total plasma calcium and magnesium concentrations of blood returning to the patient are equivalent to the concentrations entering the extracorporeal circuit. Another advantage is that the invention adjusts its control algorithms according to whether excess trisodium citrate is present in the circuit.

Another advantage is that the system may provide a health care professional with instantaneous data regarding flow rates, blood chemistry, and electrolyte levels on a convenient real-time display. A technician may therefore evaluate conditions and initiate manual adjustment of treatment parameters, as desired. By using a control system according to the invention, a technician may compare the consequences of optimized treatment parameters on plasma concentration of blood returning to the patient, or compare the consequences of automated treatment parameters controlled by software. Results may also be recorded in system memory, to collect historical data for proving optimization. The technician may also optimize treatment for specific cases in this manner. For example, parameters may need to be manually adjusted or manually input to the automatic control system to optimize treatment based on patient weight, gender, or other physical characteristics or infirmities.

The invention has been disclosed in an illustrative style. Accordingly, the terminology employed throughout should be read in an exemplary rather than a limiting manner. Although minor modifications of the present invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

The invention claimed is:

1. A blood filtration system comprising:
a filtration circuit including a filter having a dialysis solution chamber;
a blood pump configured to pump blood through the filter to produce filtered blood;
a source of citrate anticoagulant solution having a predetermined citrate anticoagulant solution concentration;
a source of electrolyte solution;
a citrate anticoagulant pump positioned and arranged to pump a citrate anticoagulant solution from the source of citrate anticoagulant solution into the filtration circuit;
a dialysis solution pump positioned and arranged to pump a citrate laden dialysis solution into the dialysis solution chamber of the filter;
an electrolyte pump positioned and arranged to pump an electrolyte solution from the source of electrolyte solution into the filtered blood; and
a controller configured to control the citrate anticoagulant pump according to an algorithm that takes into account at least:
(i) a blood flow rate,
(ii) a concentration of the citrate anticoagulant solution, and
(iii) a concentration of the electrolyte solution.

2. The blood filtration system of claim 1, wherein the controller further includes:
a processor; and
software, executable by the processor, for determining a rate of the citrate anticoagulant pump flow.

3. The blood filtration system of claim 1, which includes an electrolyte sensor that detects concentration in the blood flow of an ion selected from the group consisting of bicarbonate, calcium, chloride, copper, glucose, iron, magnesium, manganese, phosphate, potassium, sodium, and zinc, wherein the controller is in communication with the electrolyte sensor.

4. The blood filtration system of claim 3, wherein the algorithm includes a citrate pump flow rate, E, according to $E(A, B, C, D) = A \times (B + D)/C$, where A is a detected blood flow rate, B is calcium ion concentration detected by the electrolyte sensor, C is concentration of the citrate solution, and D is magnesium ion concentration detected by the electrolyte sensor.

5. The blood filtration system of claim 1, wherein the citrate anticoagulant solution has a selected citric acid concentration and a selected trisodium citrate concentration, and wherein the controller controls the citrate pump as a function of a detected blood flow, a sensed electrolyte concentration, the selected citric acid concentration, and the selected trisodium citrate concentration.

6. The blood filtration system of claim 5, wherein the algorithm includes a citrate pump flow rate, E, according to $E(A, B, C, D, G) = A \times (B+D)/(C+G)$, where A is a detected blood flow rate, B is a detected calcium ion concentration, C is the selected citric acid concentration, D is a detected magnesium ion concentration, and G is the selected-trisodium citrate concentration.

7. The blood filtration system of claim 1, which further includes:
 a blood flow detector for detecting a flow of blood from the patient; and
 a sensor for detecting fluid loss rate in the blood filtration circuit, wherein:
  (i) the electrolyte solution has a selected calcium ion concentration and a selected magnesium ion concentration, and
  (ii) the controller controls the flow from the electrolyte pump as a function of a detected blood flow rate, the detected fluid loss rate, the selected calcium ion concentration, and the selected magnesium ion concentration.

8. The blood filtration system of claim 7, wherein the controller includes a processor, and software executable by the processor for determining a desired citrate pump flow rate and a desired electrolyte pump flow rate, and for calculating an ultrafiltration rate as a function of the detected fluid loss rate, the desired citrate pump flow rate, and the desired electrolyte pump flow rate.

9. The blood filtration system of claim 8, wherein the citrate anticoagulant solution includes a selected trisodium citrate concentration, the system further including;
 a substitution solution having a selected sodium concentration;
 a substitution solution pump positioned and arranged to pump the substitution solution to supplement the blood flow; and
 a sensor for detecting substitution solution flow rate, wherein the controller further determines a post-dilution flow rate as a function of the detected blood flow rate, the selected trisodium citrate concentration; the calculated ultrafiltration rate, the selected sodium concentration of the substitution solution, and the detected substitution solution flow rate.

10. The system of claim 1, which is configured to use the citrate anticoagulant solution to supplement the blood flow as a pre-dilution solution in the blood filtration circuit.

11. The system of claim 1, wherein the citrate anticoagulant solution enters the blood filtration circuit as part of a dialysate.

* * * * *